United States Patent
Honda

(10) Patent No.: US 8,715,163 B2
(45) Date of Patent: May 6, 2014

(54) ELECTRONIC APPARATUS WITH NOISE SHIELDING

(75) Inventor: Takemitsu Honda, Hino (JP)

(73) Assignee: Olympus Corporation, Tokyo (JP)

( * ) Notice: Subject to any disclaimer, the term of this patent is extended or adjusted under 35 U.S.C. 154(b) by 1927 days.

(21) Appl. No.: 11/631,144

(22) PCT Filed: Sep. 20, 2005

(86) PCT No.: PCT/JP2005/017281
§ 371 (c)(1),
(2), (4) Date: Dec. 28, 2006

(87) PCT Pub. No.: WO2006/033323
PCT Pub. Date: Mar. 30, 2006

(65) Prior Publication Data
US 2008/0294005 A1    Nov. 27, 2008

(30) Foreign Application Priority Data
Sep. 21, 2004   (JP) ................................ 2004-273981

(51) Int. Cl.
*A61B 1/00*    (2006.01)
(52) U.S. Cl.
USPC .......................................................... 600/103
(58) Field of Classification Search
USPC .................... 174/51, 521, 549; 343/850–851; 361/796, 800; 455/296, 300, 310; 600/134, 302
See application file for complete search history.

(56) References Cited

U.S. PATENT DOCUMENTS

| | | | |
|---|---|---|---|
| 5,124,889 A | | 6/1992 | Humbert et al. |
| 5,371,404 A | | 12/1994 | Juskey et al. |
| 5,564,096 A | * | 10/1996 | Hama et al. ................... 455/300 |
| 5,777,856 A | | 7/1998 | Phillips et al. |
| 5,974,095 A | * | 10/1999 | Kitaura et al. ................ 375/340 |
| 6,058,000 A | | 5/2000 | Koenck et al. |

(Continued)

FOREIGN PATENT DOCUMENTS

| CN | 1442033 A | 9/2003 |
|---|---|---|
| CN | 1473545 A | 2/2004 |

(Continued)

OTHER PUBLICATIONS

Japanese Official Action dated May 25, 2010 together with an English language translation.

(Continued)

*Primary Examiner* — Philip R Smith
(74) *Attorney, Agent, or Firm* — Scully, Scott, Murphy & Presser, P.C.

(57) ABSTRACT

A processing device (2) includes an analog circuit block (6), a digital circuit block (7), a casing (12) which houses elements including (6) and (7) and serves as a conductive shield member, and a connecting connector (13) which has functions, for example, of electrically connecting the casing (12) and a first ground terminal (6a) provided in the analog circuit block (6). Level of noise signals generated from the analog circuit block (6) is lower than the level of noise signals generated from the digital circuit block (7). Therefore, when the casing (12) is electrically connected to the first ground terminal (6a) provided in the analog circuit block (6), the casing (12) can maintain a stable potential thereby more effectively working as the conductive shield member. Thus, leakage of the noise signals generated at driving of internal electronic circuitry is effectively suppressed in an electronic apparatus such as a receiving apparatus.

4 Claims, 8 Drawing Sheets

(56) References Cited

U.S. PATENT DOCUMENTS

| | | | |
|---|---|---|---|
| 6,522,291 | B1 | 2/2003 | Noguchi et al. |
| 6,760,610 | B2 | 7/2004 | Tschupp et al. |
| 2002/0071940 | A1 | 6/2002 | Arnold et al. |
| 2002/0117318 | A1* | 8/2002 | Suzuki ............................ 174/51 |
| 2002/0117970 | A1 | 8/2002 | Aida |
| 2003/0085994 | A1 | 5/2003 | Fujita et al. |
| 2003/0113120 | A1 | 6/2003 | Ohe et al. |
| 2003/0175454 | A1 | 9/2003 | Lichtenstein et al. |
| 2003/0210203 | A1* | 11/2003 | Phillips et al. ................. 343/850 |
| 2005/0045358 | A1* | 3/2005 | Arnold ............................ 174/51 |

FOREIGN PATENT DOCUMENTS

| | | |
|---|---|---|
| JP | S63-179614 | 11/1988 |
| JP | H1-166937 | 11/1989 |
| JP | H03-136636 | 6/1991 |
| JP | HEI3-195094 | 8/1991 |
| JP | 5-291778 | 11/1993 |
| JP | HEI7-3195 U | 1/1995 |
| JP | HEI8-288686 | 11/1996 |
| JP | H09-135832 | 5/1997 |
| JP | 10-197662 | 7/1998 |
| JP | 2000-022379 | 1/2000 |
| JP | 2000-341029 | 12/2000 |
| JP | 2001-168625 | 6/2001 |
| JP | 2001-230629 | 8/2001 |
| JP | 2002-050974 | 2/2002 |
| JP | 2003-019111 A | 1/2003 |
| JP | 2003-179377 | 6/2003 |
| JP | 2004-179255 | 6/2004 |
| WO | 95/31048 | 11/1995 |
| WO | WO 01/82672 A1 | 11/2001 |
| WO | 2004/077906 A1 | 9/2004 |

OTHER PUBLICATIONS

English language abstract of Japanese Patent Application Publication No. JP2001-230629A.

Extended Supplementary European Search Report dated Sep. 14, 2009.

European Official Action dated Dec. 29, 2010.

Japanese Official Action dated Aug. 3, together with an English translation.

* cited by examiner

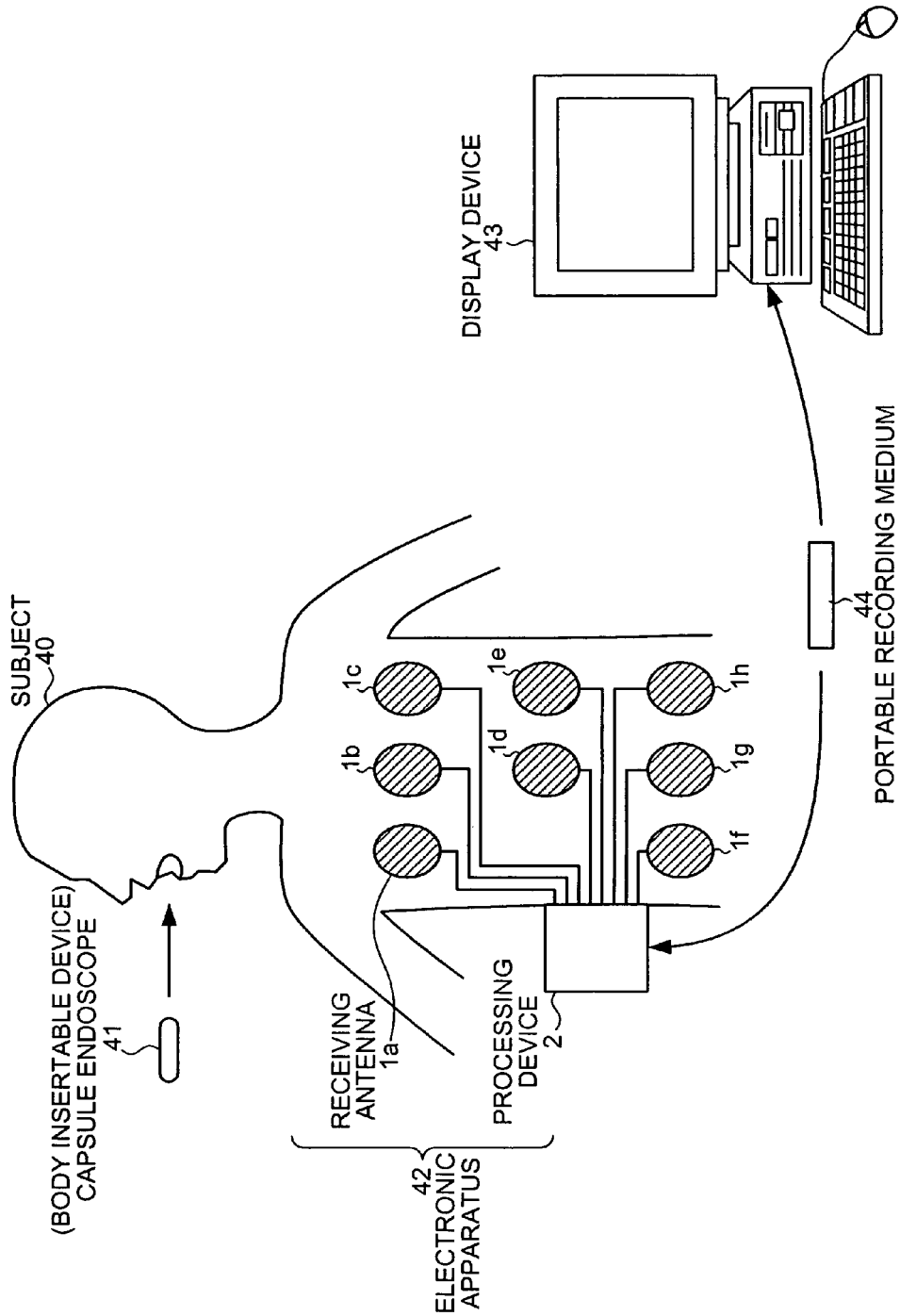

ELECTRONIC APPARATUS WITH NOISE SHIELDING

TECHNICAL FIELD

The present invention relates to an electronic apparatus which includes plural circuit blocks, and a body insertable apparatus system which includes a receiving apparatus including plural circuit blocks.

BACKGROUND ART

In recent years, a swallowable capsule endoscope has been proposed in a field of endoscope. The capsule endoscope is equipped with an imaging function and a radio communication function. After being swallowed by a subject (human body) from the mouth for an observation (examination), the capsule endoscope travels through body cavities, e.g., internal organs such as stomach and small intestine, following peristaltic movements and sequentially captures images until naturally discharged.

While traveling inside the body cavities, the capsule endoscope captures image data inside the subject and sequentially transmits the image data to an outside via radio communication. A receiving apparatus arranged outside the subject receives the image data and stores the same after predetermined processing. The subject carries and uses the receiving apparatus which has a reception mechanism, a signal processing mechanism, and a storage mechanism, therefore, the subject can move freely after swallowing the capsule endoscope until discharging the same. In a conventional capsule endoscope system, a doctor and a nurse make diagnosis after the capsule endoscope is discharged, by looking at organ images displayed on a screen based on the image data accumulated in a memory.

Patent Document 1: Japanese Patent Application Laid-Open No. 2003-19111

DISCLOSURE OF INVENTION

Problem to be Solved by the Invention

In the conventional capsule endoscope system, however, the receiving apparatus has a difficulty in securely receiving radio signals transmitted from the capsule endoscope. In the conventional capsule endoscope system, the receiving apparatus receives not only the radio signals but also noise signals generated by electromagnetic radiation emitted by an electronic circuit arranged in the receiving apparatus when the electronic circuit is driven. Therefore, a Carrier to Noise (CN) ratio of the received radio signals is decreased.

Since the capsule endoscope performs radio transmission while the capsule endoscope is inside the subject, strength of the radio signals is set to an extremely low level to minimize negative influences on the human body, for example. In addition, the radio signals generally have a property of being attenuated while passing through a body tissue such as an internal organ. Therefore, when the radio signals transmitted from the capsule endoscope system reaches a receiving antenna, the signal level thereof is even lower, whereas the influence of the noise signals increases relatively in comparison. Hence, the control of electromagnetic radiation is particularly significant in the receiving apparatus employed in the capsule endoscope system.

For example, it may be possible to form an outer casing of the receiving apparatus partly from a conductive material so as to shield the electromagnetic radiation. Specifically, the outer casing which works as a shield member electrically separates an electronic circuit arranged in the outer casing from a space outside the receiving apparatus, and keeps the noise signals generated by the driven electronic circuit inside the receiving apparatus, whereby the noise signals are prevented from reaching a receiving antenna arranged outside the outer casing.

When the above structure is adopted, however, it is difficult to provide a suitable potential supply source for supplying a ground potential to the shield member in the receiving apparatus, particularly in the receiving apparatus of the capsule endoscope system. In the capsule endoscope system as described above, the subject carries around the receiving apparatus during its use. Hence, the potential supply source of the shield member must be provided inside the receiving apparatus. Incorporation of a large potential supply source inside the receiving apparatus results in an increase in the size of the receiving apparatus, and is particularly inappropriate for an apparatus like the receiving apparatus which is employed in the capsule endoscope system and is required to be portable.

In view of the foregoing, an object of the present invention is to provide an electronic apparatus, such as a receiving apparatus, in which noise signals generated at driving of internal electronic circuitry are effectively prevented from leaking out.

Means for Solving Problem

An electronic apparatus according to one aspect of the present invention is provided with plural circuit blocks, and includes a first circuit block which has at least a predetermined first ground terminal and receives a ground potential via the first ground terminal; a second circuit block which has at least a second ground terminal, receives the ground potential via the second ground terminal, and generates a noise signal of a level higher than a level of a noise signal of the first circuit block on being driven; and a conductive shield member which receives the ground potential via the first ground terminal.

According to this electronic apparatus, since the shield member is electrically connected to the first ground terminal of the first circuit block which generate low level noise signals, the potential of the shield member is stable, and the noise signals generated by the first circuit block and the second circuit block can be effectively shielded.

Further, in the electronic apparatus, the first circuit block may be an analog circuit block that performs analog processing, and the second circuit block may be a digital circuit block that performs digital processing.

Further, in the electronic apparatus, the conductive shield member may be configured to house the first circuit block and the second circuit block inside, and the electronic apparatus may further include a receiving antenna arranged outside the conductive shield member, wherein the first circuit block and the second circuit block may perform predetermined processing on a radio signal received by the receiving antenna.

Further, in the electronic apparatus, the conductive shield member may be integrally formed with a casing which houses the first circuit block and the second circuit block.

Further, in the electronic apparatus, the casing may include a case member which is configured to be hollow inside and which defines an outer shape of the casing, a conductive coating layer which is formed with a coating of a conductive paint on an inner surface side of the case member, and a protective layer which is arranged between an inner surface of the case member and the conductive coating layer.

Further, in the electronic apparatus, the first circuit block and the second circuit block may be formed on at least one board, and the electronic apparatus may further include an insulating mold layer which is arranged so as to cover the board, the first circuit block, and the second circuit block, wherein the conductive shield member may be formed with a conductive mold layer formed on the insulating mold layer and electrically connected to the first terminal.

Further, a body insertable apparatus system according to another aspect of the present invention includes a body insertable device which is introduced inside a subject, acquires intra-subject information, and transmits radio signals containing the intra-subject information to an outside; and a receiving apparatus which receives the radio signals transmitted from the body insertable device. The receiving device includes a first circuit block provided at least with a predetermined first ground terminal, a second circuit block provided at least with a second ground terminal and generating a noise signal of a level higher than a level of a noise signal of the first circuit block on being driven, and a shield member which receives a ground potential via the first ground terminal.

Further, in the body insertable apparatus system, the first circuit block may perform analog processing, and the second circuit block performs digital processing.

Effect of the Invention

Since the electronic apparatus and the receiving apparatus in the body insertable apparatus system according to the present invention include the shield member which is electrically connected to the first ground terminal provided in the first circuit block which generates low level noise signals, the potential of the shield member is stable, whereby the noise signals generated from the first circuit block and the second circuit block are effectively shielded.

BRIEF DESCRIPTION OF DRAWINGS

FIG. 9 is a schematic diagram of an overall structure of a body insertable apparatus system according to a second embodiment.

EXPLANATIONS OF LETTERS OR NUMERALS

Figure 1:
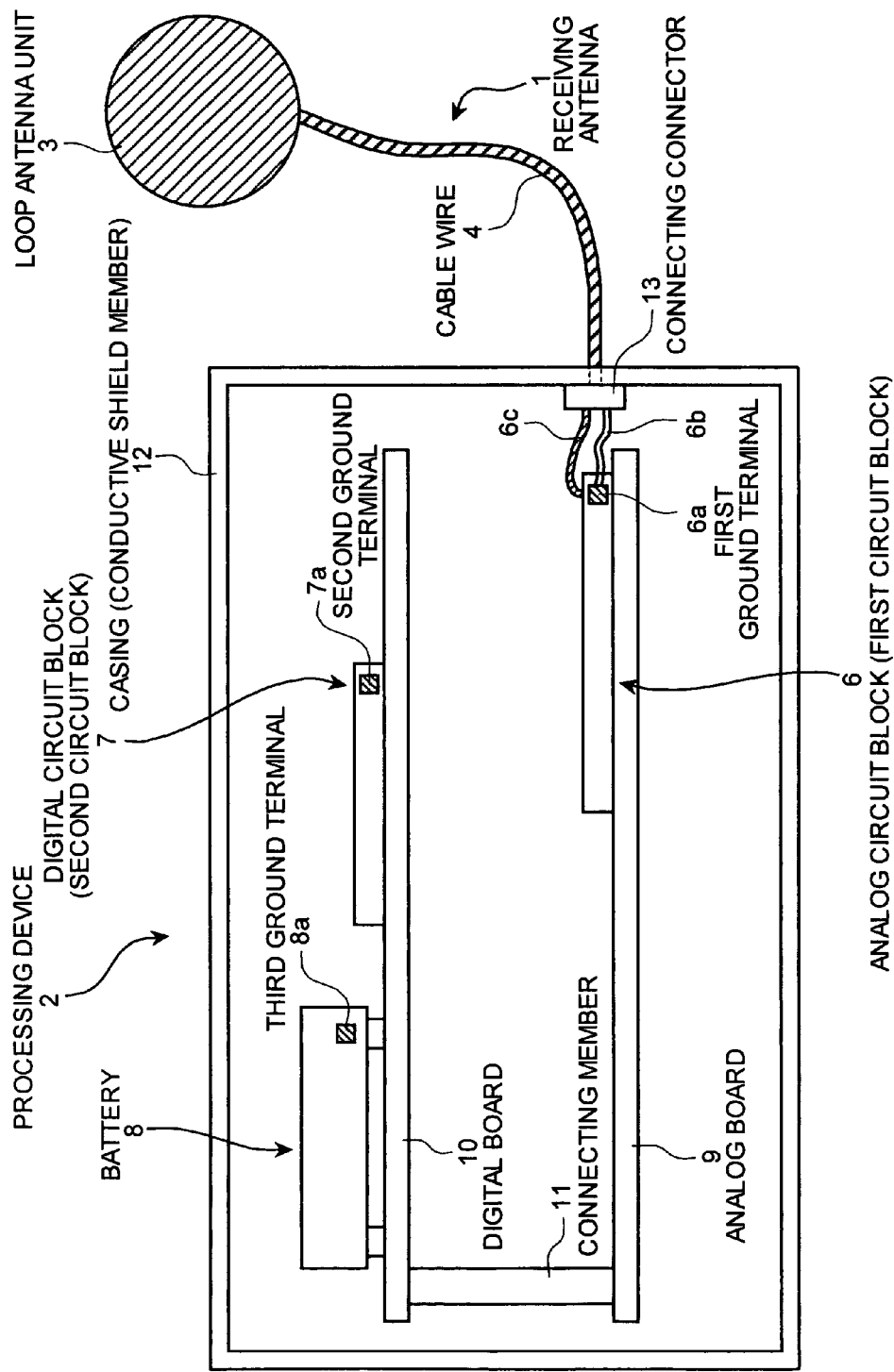
FIG. 1 is a schematic diagram of a structure of an electronic apparatus according to a first embodiment.

1 Receiving antenna
2 Processing device
3 Loop antenna unit
4 Cable wire
6 Analog circuit block
6a First ground terminal
6b, 6c Wire
7 Digital circuit block
7a Second ground terminal
8 Battery
8a Third ground terminal
9 Analog board
10 Digital board
11 Connecting member
12, 20, 27 Casing
12a Case member
12b Protective layer
12c Conductive coating layer
13, 24 Connecting connector
13a Contact
13b Coaxial cable
13c Connecting cable
13d Insulating region
13e Conductive portion
13f Coated portion
15 Terminal
16 Harness
17, 18 Screw
19 Processing device
21 Circuit board
22 Insulating mold layer
23 Conductive mold layer
28 Button
29 Opening
30 Switch board
31 Sensor unit
32, 36 Supporting member
33 Conductive rubber sheet
35 Conductive shield board
37 Wire
40 Subject
41 Capsule endoscope
42 Electronic apparatus
43 Display device
44 Portable recording medium

BEST MODE(S) FOR CARRYING OUT THE INVENTION

Exemplary embodiments of an electronic apparatus and a body insertable apparatus system including the electronic apparatus will be described below. It should be noted that the present invention is not limited to the embodiments. The drawings are merely schematic, and the ratio between the thickness and width in each portion or the ratio of thickness of one portion to another may be different in an actual apparatus or system. The dimensional relation and the ratio may be different from one drawing to another. In the following, a receiving apparatus will be described as an example of the electronic apparatus. It should be apparent from below, however, that the present invention is applicable to any electronic apparatus other than the receiving apparatus.

First Embodiment

First, an electronic apparatus according to a first embodiment will be described. FIG. 1 is a schematic diagram of an overall structure of the electronic apparatus according to the first embodiment. As shown in FIG. 1, the electronic apparatus according to the first embodiment includes a receiving antenna 1 which is employed to receive radio signals, and a processing device 2 which performs predetermined processing on the radio signals received by the receiving antenna 1.

The receiving antenna 1 includes a loop antenna unit 3 which is employed to receive the radio signals, and a cable wire 4 which serves to transmit signals received by the loop antenna unit 3 to a circuit or the like in a casing 12. The loop antenna unit 3 consists of, for example, a film-like base material and a spiral-shaped conductive wire placed on a surface of the base material. The loop antenna unit 3 receives the radio signals by the spiral-shaped portion. The cable wire 4 serves to electrically connect the loop antenna unit 3 with the processing device 2 (more precisely, with a connecting connector 13 of the processing device 2). The cable wire 4 is made of a flexible cable, for example.

The above described structure is, as described later, appropriate for the use of the electronic apparatus according to the first embodiment in a body insertable apparatus system. In the body insertable apparatus system, it is preferable that an antenna portion be arranged on a body surface of the subject in close contact therewith so that low-level radio signals transmitted from the capsule endoscope in the subject can be securely received. In the receiving antenna 1, the loop antenna unit 3, which is employed for the reception of the radio signals substantially, includes the film-like member as the base material. The film-like member can be readily attached to the body surface of the subject in close contact with the subject even though the body surface is not smooth. Further, the cable wire 4 is formed with the flexible member, so that the loop antenna unit 3 can be secured at any position on the body surface.

The processing device 2 serves to perform processing such as reception of the radio signals received by the receiving antenna 1, more particularly by the loop antenna unit 3. Specifically, the processing device 2 includes an analog circuit block 6 which perform analog processing, a digital circuit block 7 which perform digital processing, and a battery 8 which supplies driving power to the analog circuit block 6 and the digital circuit block 7. Further, the processing device 2 includes an analog board 9 which supports the analog circuit block 6, a digital board 10 which supports the digital circuit block 7 and the battery 8, and a connecting member 11 which serves to define positional relation between the analog board 9 and the digital board 10 and to electrically connect the analog board 9 and the digital board 10. Further, the processing device 2 includes a casing 12 which houses the above mentioned elements, and the connecting connector 13 which is housed in the casing 12 and has functions, for example, of electrically connecting the casing 12 and a first ground terminal 6a (described later) in the analog circuit block 6.

The analog circuit block 6 is an example of a first circuit block of the present invention. Specifically, the analog circuit block 6 serves to perform analog processing on predetermined signals (in the first embodiment, radio signals received by the receiving antenna 1), and includes an electric circuit and the like required for the processing. Specifically, the analog circuit block 6 has functions, for example, of performing processing such as demodulation on the received radio signals, and of extracting a predetermined original signal contained in the radio signals. Further, the analog circuit block 6 includes the first ground terminal 6a for supplying the ground potential to a circuit structure provided in the analog circuit block 6. The first ground terminal 6a may generate the ground potential by itself, or may be electrically connected to another potential supply source and supply the ground potential generated by the potential supply source into the internal circuitry.

The first ground terminal 6a provided in the analog circuit block 6 has a function of supplying the ground potential to the casing 12 which works as a conductive shield member as described later. Specifically, as shown in FIG. 1, the first ground terminal 6a is electrically connected to the casing 12 via a wire 6b and the connecting connector 13 (described later). Further, the analog circuit block 6 includes a wire 6c through which the radio signals received by the receiving antenna 1 are supplied. The wire 6c is electrically connected to the cable wire 4 of the receiving antenna 1 via the connecting connector 13. A specific manner of electrical connection between the analog circuit block 6 and each of the casing 12 and the cable wire 4 is not detailed here, and will be described as a part of the description of the connecting connector 13.

The digital circuit block 7 is an example of a second circuit block of the present invention. Specifically, the digital circuit block 7 has functions of, for example, digitizing analog signals supplied from the analog circuit block 6 and performing digital processing on the digitized signals, and includes an electronic circuit and the like required for such processing. For example, when the electronic apparatus works as the receiving apparatus as in the first embodiment, the digital circuit block 7 serves to reconfigure image data, for example, based on the original signals extracted by the analog circuit block 6. Further, the digital circuit block 7, similarly to the analog circuit block 6, includes a second ground terminal 7a for supplying the ground potential to an electronic circuit in the digital circuit block 7. The battery 8 has a similar structure, and includes a third ground terminal 8a for supplying the ground potential. In FIG. 1, the first ground terminal 6a and the like are drawn as if being arranged on a side surface of the analog circuit block 6 and the like, merely for the convenience of the formulation of the drawing. In practice, the elements such as the first ground terminal 6a can be arranged at any position, for example, on an upper surface of the analog circuit block 6. The same applies to other drawings. In the first embodiment, the term "terminal" means a member which is electrically connected to other member, and the term covers a broad concept including a member of any structure other than a pad-like shape.

The analog board 9 and the digital board 10 serve to support the analog circuit block 6, and the digital circuit block 7 and the battery 8, respectively. Each of the analog board 9 and the digital board 10 has printed wiring on a surface thereof, and the analog board 9 and the digital board 10 have a function of electrically connecting the analog circuit block 6, and the digital circuit block 7 and the battery 8 with each other in combination with an effect of the connecting member 11.

The casing 12 which houses the above mentioned elements will be described below. The casing 12 works as a case member for protecting the analog circuit block 6, the digital circuit block 7, and the like from a physical impact applied from outside, and at the same time serves as an example of the conductive shield member of the present invention.

Figure 2:
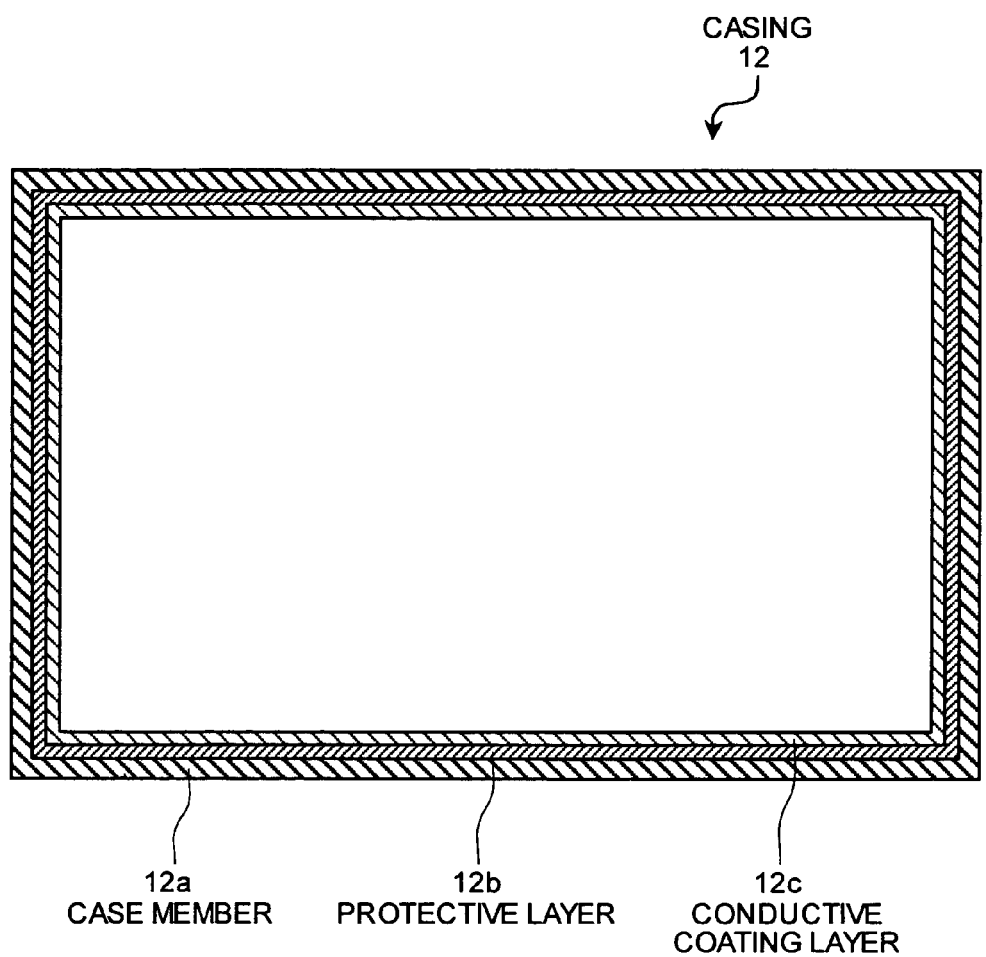
FIG. 2 is a schematic diagram of a specific structure of a casing of the electronic apparatus.

FIG. 2 is a schematic sectional view of a structure of the casing 12. As shown in FIG. 2, the casing 12 includes a case member 12a formed from a molded resin material, for example, a protective layer 12b which is formed on an inner surface of the case member 12a, and a conductive coating layer 12c which is formed from a conductive coating material applied on an inner surface of the protective layer 12b.

The case member 12a is provided so that the casing 12 works as a proper casing. Specifically, the case member 12a has functions of physically separating the analog circuit block 6 and the like housed in the casing 12 from an outer space, and protecting the analog circuit block 6 and the like from impacts applied from outside.

The conductive coating layer 12c is provided so that the casing 12 works as the conductive shield member. Specifically, the conductive coating layer 12c is formed from the conductive coating material applied on an entire inner surface of the case member 12a (more strictly, an inner surface of the protective layer 12b formed on the inner surface of the case member 12a), and has a function of electrically shielding the analog circuit block 6 and the like from the outer space. In the following description, when the casing 12 is referred to as the conductive shield member, the conductive coating layer 12c in the casing 12 will be focused in particular.

The protective layer 12b serves to protect the case member 12a from the conductive coating layer 12c. Specifically, the conductive coating material of the conductive coating layer 12c is generally a solution of a metal material dissolved in a predetermined solvent. The solvent may act on the case member 12a itself and corrode the resin material of the case member 12a, for example. Therefore, in the first embodiment, the protective layer 12b is placed between the conductive coating layer 12c and the case member 12a to prevent the corrosion or the like of the case member 12a, and the conductive coating layer 12c is prevented from acting on the case member 12a. Any material can be employed as a material of the protective layer 12b. In consideration of the function of the protective layer 12b as described above, however, it is preferable that a material which is inactive against the conductive coating material of the conductive coating layer 12c be employed.

The connecting connector 13 will be described. The connecting connector 13 serves to electrically connect the first ground terminal 6a provided in the analog circuit block 6 with the casing 12. Specifically, the connecting connector 13 serves to supply the ground potential to the conductive coating layer 12c provided in the casing 12 when the casing 12 works as the conductive shield member.

Figure 3:
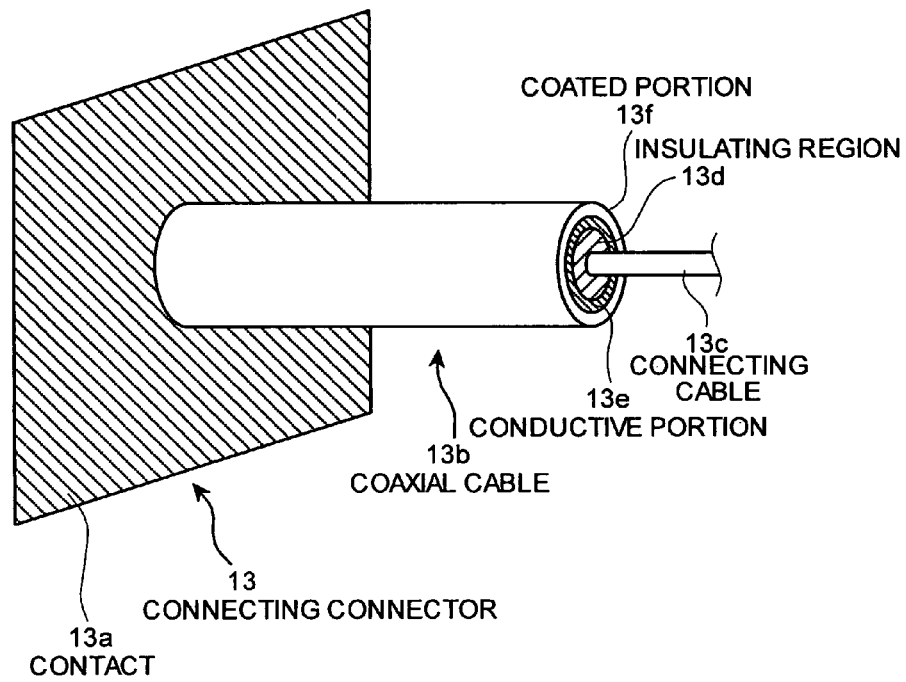
FIG. 3 is a schematic diagram of a specific structure of a connecting connector housed in the casing.

FIG. 3 is a schematic diagram of a specific structure of the connecting connector 13. As shown in FIG. 3, the connecting connector 13 includes a contact 13a which is formed with a plate-like conductive material and physically contacts with an inner surface of the casing 12 (more precisely, an inner surface of the conductive coating layer 12c), and a coaxial cable 13b which extends in a direction of a normal line with respect to a main plane of the contact 13a to electrically connect to the receiving antenna 1. The coaxial cable 13b is symmetrical about a central axis. The coaxial cable 13b includes a connecting cable 13c arranged on the central axis thereof, and an insulating region 13d, a conductive portion 13e, and a coated portion 13f, sequentially arranged radially from the center in this order.

The connecting cable 13c is electrically connected to the cable wire 4 of the receiving antenna 1, and serves to transmit the radio signals received by the receiving antenna 1 to the analog circuit block 6. Hence, the connecting cable 13c is electrically connected to the wire 6c at its proximal end side.

The conductive portion 13e serves to supply the ground potential to the loop antenna unit 3. The ground potential can be supplied from any elements, though in the embodiment, the conductive portion 13e is electrically connected to the first ground terminal 6a, similarly to the casing 12.

The insulating region 13d serves to electrically insulate the connecting cable 13c from the conductive portion 13e. Specifically, the insulating region 13d is formed with a resin material such as a plastic, and arranged in a region between the connecting cable 13c and the conductive portion 13e, so as to have a function of electrically insulating the connecting cable 13c from the conductive portion 13e. Further, the coated portion 13f serves to protect the conductive portion 13e from the outside, and is made from a flexible vinyl material, for example.

The contact 13a is arranged so as to be in a physical contact with the casing 12 (more precisely, the conductive coating layer 12c) so that the contact 13a is in an electrical contact with the conductive coating layer 12c, whereby the contact 13a has a function of supplying the ground potential of the first ground terminal 6a to the conductive coating layer 12c. In order to realize such a function of the contact 13a, the contact 13a is electrically connected to the first ground terminal 6a via the wire 6b.

Further, the contact 13a is fixed to the casing 12 in such a manner that the main plane of the contact 13a is in close contact with the conductive coating layer 12c. A manner of fixation may be, for example, a bonding with a conductive bonding agent, or a fixation with a screw which is fitted into a screw hole formed in advance. When the contact 13a is fixed so that the main plane of the contact 13a is in close contact with the inner surface of the conductive coating layer 12c, an area of the contact 13a in contact with the conductive coating layer 12c can be increased so as to reduce an electrical contact resistance.

Figure 4:
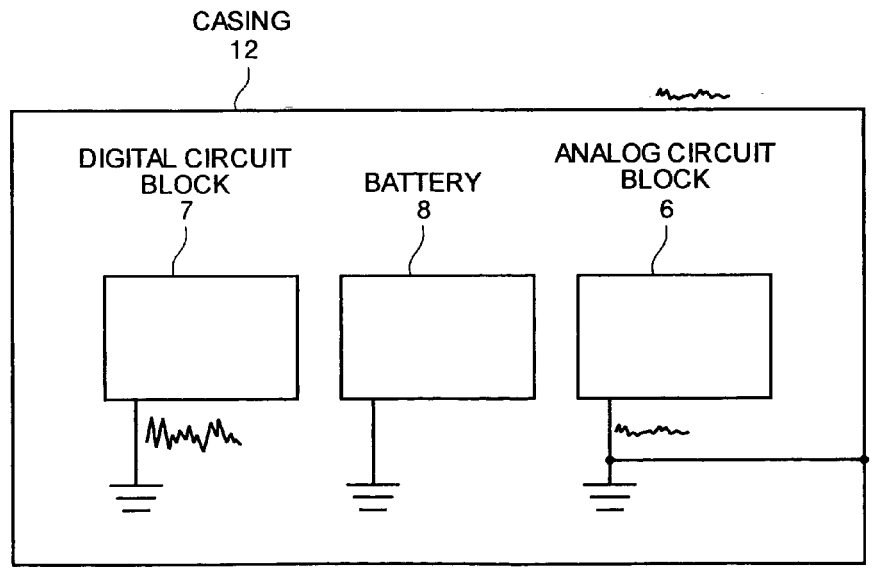
FIG. 4 is a schematic diagram describing a function of the casing as a conductive shield member.

A function of the electronic apparatus according to the first embodiment, whereby the electromagnetic radiation generated from the internal circuitry is prevented, will be described. FIG. 4 is a schematic diagram describing such a function. As shown in FIG. 4, in the electronic apparatus according to the first embodiment, an electrically predetermined ground potential is supplied to each of the analog circuit block 6, the digital circuit block 7, and the battery 8. On the other hand, the ground potential of the analog circuit block 6 is supplied to the casing 12. Since a substantially constant ground potential is supplied to the casing 12, the analog circuit block 6, the digital circuit block 7, and the battery 8 are electrically blocked from the outside space of the casing 12, whereby the noise signals generated from the digital circuit block 7 and the like is prevented from propagating to the outside.

In the first embodiment, the casing 12 is electrically connected to the first ground terminal 6a of the analog circuit block 6 as described earlier. Therefore, the ground potential of the casing 12 is equal to the potential of the first ground terminal 6a, hence is equal to the ground potential of the analog circuit block 6. In the first embodiment, the noise signal generated in the analog circuit block 6 has lower strength than the noise signal generated in the digital circuit block 7, as described earlier. Therefore, the ground potential exhibits a less fluctuation attributable to the noise signals, in comparison with the fluctuation observed in the electric apparatus in which the casing 12 is electrically connected with the second ground terminal 7a of the digital circuit block 7.

Advantages of the electronic apparatus according to the first embodiment will be described. The electronic apparatus according to the first embodiment can effectively prevent the leakage of the noise signals generated from the internal electronic circuitry with a simplified structure.

The electronic apparatus of the first embodiment is configured so that the ground potential of the casing 12 which works as the conductive shield member is equal to the ground potential of the analog circuit block 6, as described above. Since the level of the noise signal generated in the analog circuit block 6 is lower than the level of the noise signal generated in the digital circuit block 7 at the driving, the fluctuation in the potential is smaller at the first ground terminal 6a. Therefore, the fluctuation in the potential of the casing 12 is reduced in comparison with that in the electronic apparatus in which the casing 12 is electrically connected to the digital circuit block 7. Generally, it is preferable that the conductive shield member have a stable potential in order to realize its full performance. In the electronic apparatus of the first embodiment, the reduction in fluctuation of the potential of the casing 12 allows for a more effective suppression of the leakage of the noise signals generated from the digital circuit block 7 and the like to the outside of the processing device 2.

Further, in the electronic apparatus of the first embodiment, a ground potential supply source for the casing 12, which works as the conductive shield member, is not provided independently. The ground potential is supplied via the first ground terminal 6a provided in the analog circuit block 6. Therefore, it is not necessary to additionally provide a constant voltage source or the like to control the electromagnetic radiation. Thus, the electronic apparatus which prevents the leakage of the noise signals to the outside can be easily realized.

First Modification

Figure 5:
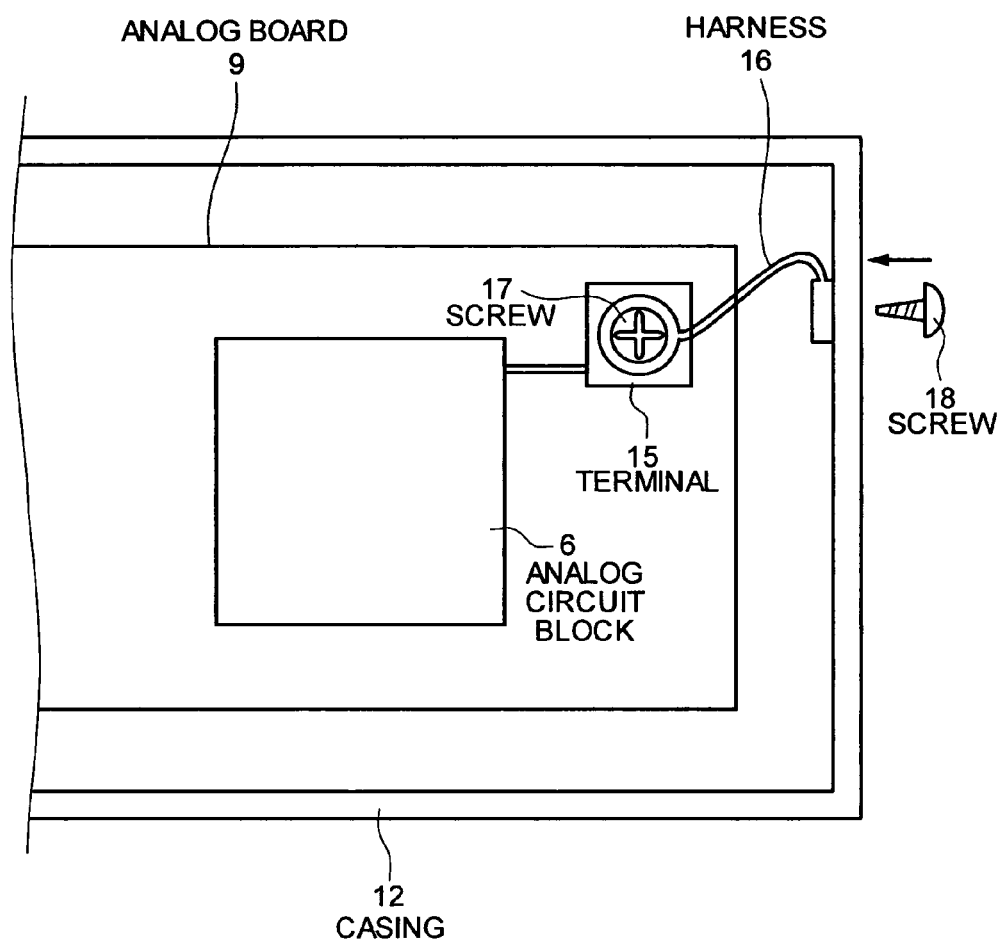
FIG. 5 is a schematic diagram of a first modification of the first embodiment.

A first modification of the electronic apparatus according to the first embodiment will be described. FIG. 5 is a schematic diagram of a part of a structure of an electronic apparatus according to the first modification. As shown in FIG. 5, a terminal 15 is arranged on the analog board 9 placed in the casing 12, and is electrically connected to the first ground terminal 6a (not shown in FIG. 5) of the analog circuit block 6.

The terminal 15 is electrically connected to the casing 12 via a harness 16, whereby the ground potential of the analog circuit block 6 is supplied to the casing 12. Specifically, a predetermined screw hole is formed in each of the terminal 15 and the casing 12 in advance. Two ends of the harness 16 are aligned with the screw holes and fixed with screws 17 and 18. Thus, the terminal 15, the casing 12, and the harness 16 are electrically connected with each other.

When the electronic apparatus has the above structure, the same advantages as those of the electronic apparatus of the first embodiment can be obtained. As far as the ground potential of the analog circuit block 6 can be supplied to the casing 12, any structure other than that of FIG. 5 can be employed for the electronic apparatus.

Second Modification

Figure 6:
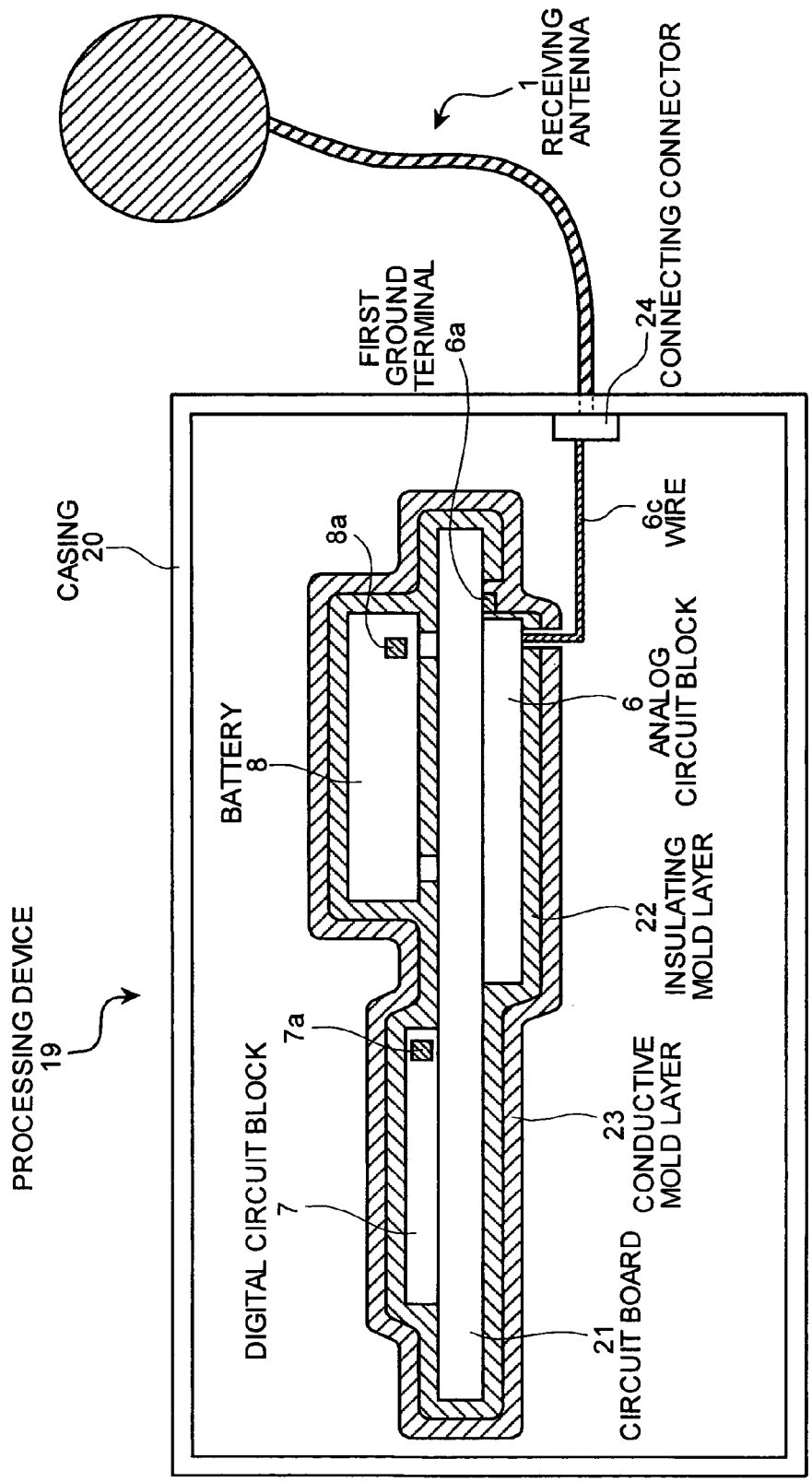
FIG. 6 is a schematic diagram of a second modification of the first embodiment.

A second modification of the electronic apparatus according to the first embodiment will be described. FIG. 6 is a schematic diagram of a structure of an electronic apparatus according to the second modification. As shown in FIG. 6, in the electronic apparatus according to the second modification, a circuit board 21 is arranged in a casing 20 of a processing device 19. The analog circuit block 6, the digital circuit block 7, and the battery 8 are arranged on the circuit board 21. The electronic apparatus of the second modification further includes an insulating mold layer 22 which is wrapped around the circuit board 21 and the analog circuit block 6 and the like arranged on the circuit board 21, and a conductive mold layer 23 which is wrapped around the insulating mold layer 22.

The insulating mold layer 22 is not wrapped around the whole of the circuit board 21 and the analog circuit block 6 or the like arranged on the circuit board 21. There is an opening region at a position corresponding to the position of each of the first ground terminal 6a and the wire 6c of the analog circuit block 6. In the conductive mold layer 23, though a predetermined opening region is formed at a position corresponding to the position of the wire 6c to prevent an electrical contact between the conductive mold layer 23 and the wire 6c, no opening region is formed at a position corresponding to the position of the first ground terminal 6a so that the conductive mold layer 23 is in electrical contact with the first ground terminal 6a.

As can be seen from the foregoing, the conductive mold layer 23 is configured to be wrapped around the circuit board 21 and the digital circuit block 7 and the like arranged on the circuit board 21 and to be electrically connected to the first ground terminal 6a. Such a structure is electrically equivalent to the structure of the casing 12 of the first embodiment. The conductive mold layer 23 of the second modification serves as another example of the conductive shield member of the present invention. Thus, the conductive shield member of the present invention may have a structure other than the structure of the casing 12 of the first embodiment. As far as the member is formed from a conductive material and is electrically connected to the first ground terminal 6a of the analog circuit block 6, any member other than that of FIG. 6 can serve as the conductive shield member.

Since the conductive mold layer 23 of the second modification serves as the conductive shield member, the casing 20 may include only the case member 12a. Further, since there is no need to electrically connect the first ground terminal 6a and the casing 20, a connecting connector 24 is required only to electrically connect the wire 6c to the receiving antenna 1.

Third Modification

A third modification of the electronic apparatus according to the first embodiment will be described. An electronic apparatus according to the third modification includes a button on the casing for controlling the driven state, for example, of the analog circuit block 6 or the like inside. Specifically, it is necessary to form a button hole to make the button work, and it is necessary to prevent the leakage of the noise signals from the button hole in order to make the casing work as the conductive shield member. In the electronic apparatus of the third modification, the casing fully functions as the conductive shield member even though the button is arranged on the casing.

Figure 7:
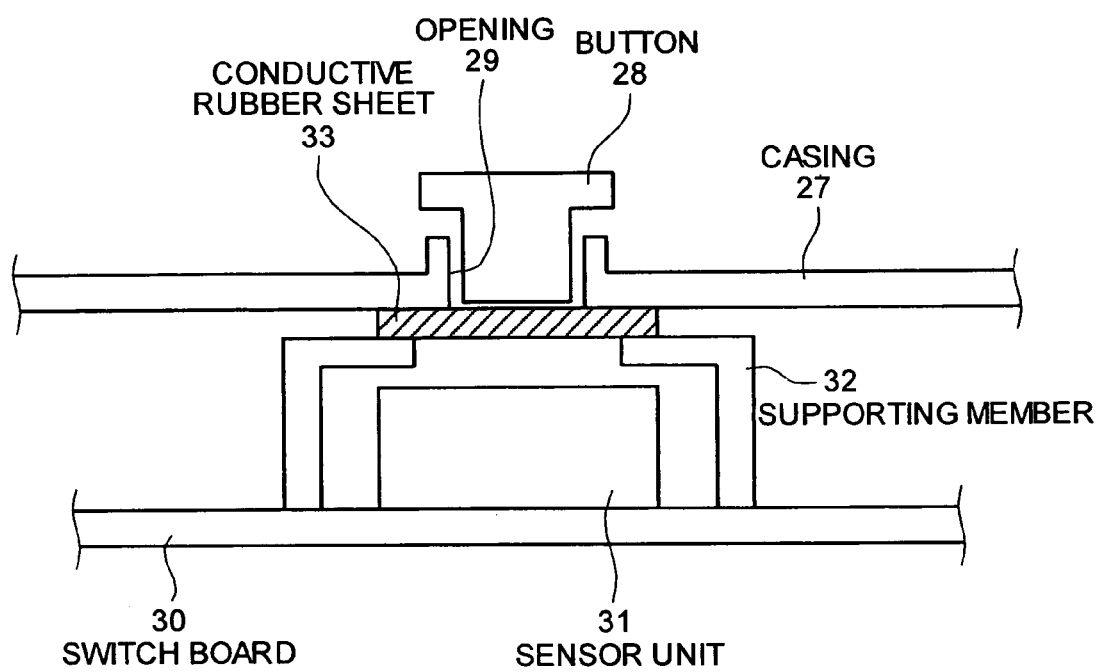
FIG. 7 is a schematic diagram of a third modification of the first embodiment.

FIG. 7 is a schematic sectional view of a structure around the button in the electronic apparatus of the third modification. As shown in FIG. 7, a casing 27, which works as the conductive shield member similarly to the first embodiment, has an opening 29 through which a button 28 is pushed into. A switch board 30 is arranged inside the casing 27 at a position corresponding to a position of the opening 29. A sensor unit 31 is arranged on the switch board 30. The sensor unit 31 works as a contact sensor. Specifically, the sensor unit 31 generates signals indicating, for example, ON and OFF, when some members touch an upper surface of the sensor unit 31, and has a function of supplying the signals to the analog circuit block 6 and the like through a wiring structure formed on the switch board 30.

Between a proximal end side of the button 28 and the upper surface of the sensor unit 31, a conductive rubber sheet 33 is arranged so as to cover the opening 29 from inside the casing 27. The conductive rubber sheet 33 is supported by a supporting member 32. In the third modification, the conductive rubber sheet 33 is sandwiched and secured between an outer surface of the supporting member 32 and an inner surface of the casing 27. A peripheral portion of the conductive rubber sheet 33 remains to be attached to the casing 27. The conductive rubber sheet 33 is made from a sheet-like member which has a conductivity and a predetermined elasticity, and is easily deformed when an external force is applied.

In the third modification, since there is the conductive rubber sheet 33, the casing 27 can function as the conductive shield member even when the opening is formed in the casing 27. Since the peripheral portion of the conductive rubber sheet 33 is fixed to the casing 27 in close contact with each other, an internal space of the casing 27 can be completely blocked from an external space of the casing 27 regardless of the presence of the opening 29. In other words, the noise signals generated by the digital circuit block 7 and the like arranged inside the casing 27 and propagating toward the opening 29 is shielded by the conductive rubber sheet 33 which is maintained at the ground potential due to the electrical connection with the casing 27, whereby the noise signals are prevented from leaking out of the casing 27.

Further, the arrangement of the conductive rubber sheet 33 does not obstruct the function of the button 28. Since the conductive rubber sheet 33 is made of a material which is easily deformed in response to a pressing force of the button 28, when a user pushes the button 28, the conductive rubber sheet 33 is deformed according to the pressing force, whereby a lower surface of the conductive rubber sheet 33 touches the upper surface of the sensor unit 31. Since the sensor unit 31 operates in response to the contact of some members on the upper surface, above described series of operations results in the generation of a predetermined signal. Thus, regardless of the presence of the conductive rubber sheet 33, the button 28 can remain functioning properly.

Fourth Modification

A fourth modification of the electronic apparatus according to the first embodiment will be described. The electronic apparatus according to the fourth modification includes, in addition to the structure of the first embodiment, a conductive shield board arranged between the analog board 9 and the digital board 10.

Figure 8:
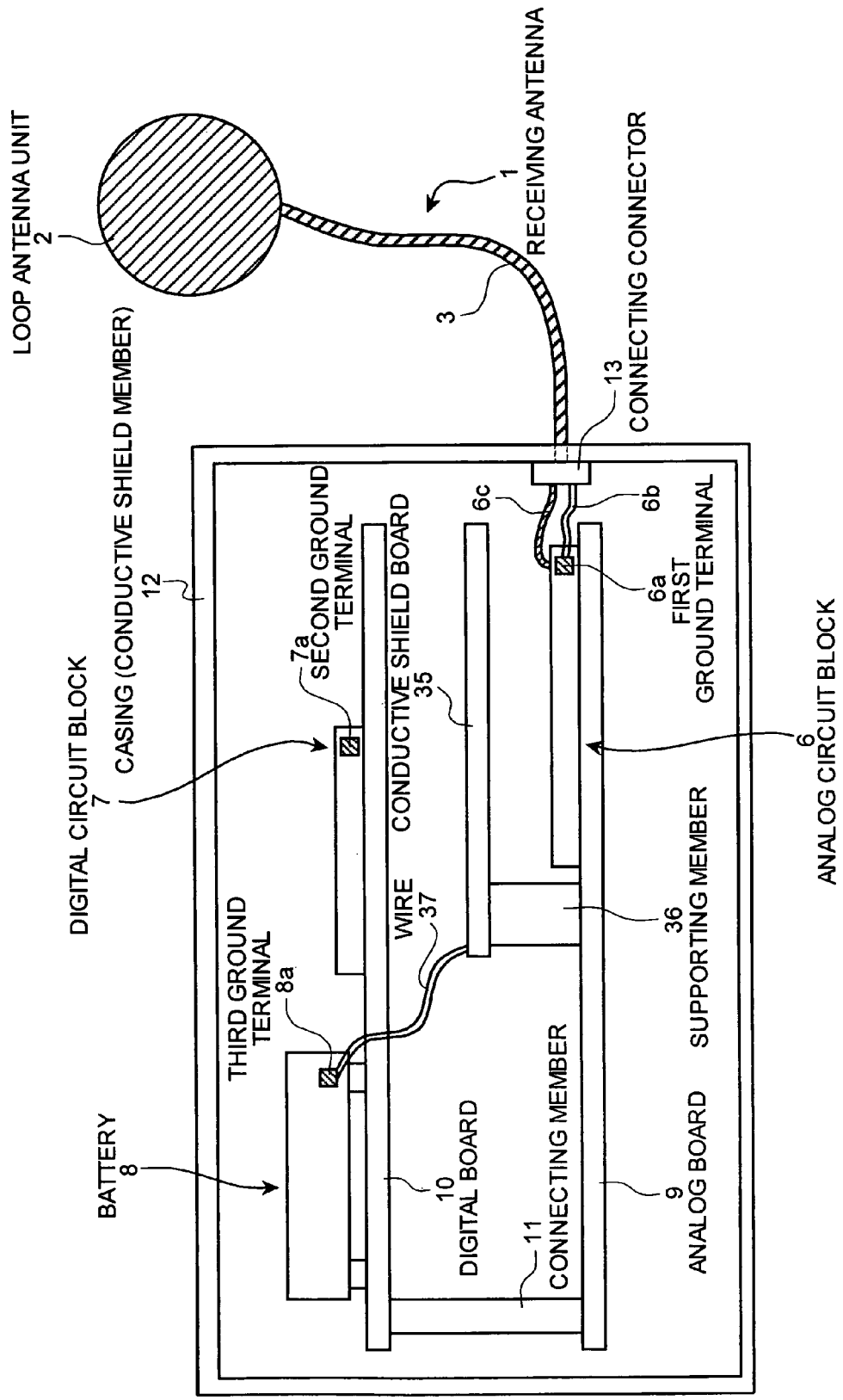
FIG. 8 is a schematic diagram of a fourth modification of the first embodiment.

FIG. 8 is a schematic diagram of a structure of the electronic apparatus according to the fourth embodiment. As shown in FIG. 8, in the electronic apparatus according to the fourth modification, a conductive shield board 35 is arranged between the analog board 9 and the digital board 10, more specifically, between the digital circuit block 7 and the analog circuit block 6. The conductive shield board 35 is fixed to the analog board 9 with a supporting member 36 arranged on the analog board 9, and is electrically connected to the third ground terminal 8a provided in the battery 8 via a wire 37.

The conductive shield board 35 is a board made of a conductive material, and works as the conductive shield member which suppress the arrival of the noise signals generated from the digital circuit block 7 at the analog circuit block 6. Specifically, the conductive shield board 35 is electrically connected to the third ground terminal 8a via the wire 37, and thereby maintained at a potential equal to the ground potential supplied by the third ground terminal 8a. Thus, the noise signals generated from the digital circuit block 7 are blocked by the conductive shield board 35, and negative influence on the operation of the analog circuit block 6 can be suppressed.

In the fourth modification, the conductive shield board 35 may be electrically connected to one of the second ground terminal 7a and the first ground terminal 6a. However, since the potential of the second ground terminal 7a fluctuates because of the influence of the noise signals generated from the digital circuit block 7, the conductive shield board 35 electrically connected to the second ground terminal 7a may exhibit deterioration in the shielding function. On the other hand, when the conductive shield board 35 is electrically connected to the first ground terminal 6a, incidence of the noise signals on the conductive shield board 35 may increase the fluctuation in the potential of the first ground terminal 6a. Therefore, it is preferable as the best embodiment that the conductive shield board 35 be electrically connected to a ground terminal other than the first ground terminal 6a and the second ground terminal 7a, in other words, to the third ground terminal 8a, for example.

Second Embodiment

A body insertable apparatus system according to a second embodiment will be described. The body insertable apparatus system according to the second embodiment includes the electronic apparatus of the first embodiment (i.e., one of the first to the fourth modifications) as a receiving apparatus.

FIG. 9 is a schematic diagram of an overall structure of the body insertable apparatus system according to the second embodiment. As shown in FIG. 9, the body insertable apparatus system according to the second embodiment includes a capsule endoscope 41 which is inserted into a subject 40 and travels along a predetermined passage, an electronic apparatus 42 which receives radio signals containing intra-subject information as transmitted from the capsule endoscope 41, a display device 43 which displays contents of the intra-subject information contained in the radio signals received by the electronic apparatus 42, and a portable recording medium 44 which serves for information delivery between the electronic apparatus 42 and the display device 43.

The capsule endoscope 41 is introduced into the subject and serves to acquire images inside the subject 40. Specifically, the capsule endoscope 41 has a small-capsule-like shape to facilitate the insertion into the subject 40, and incorporates an imaging mechanism for capturing images inside the subject and a radio transmission mechanism for transmitting the radio signals containing image data acquired by the imaging mechanism.

The portable recording medium 44 works as an external device in the present invention. Specifically, the portable recording medium 44 can be attached to and detached from the electronic apparatus 42 and the display device 43, and information can be output from or recorded into the portable recording medium 44 while the portable recording medium 44 is attached to the electronic apparatus 42 or the display device 43. While the capsule endoscope 41 travels through the body cavity of the subject 40, the portable recording medium 44 is attached to the electronic apparatus 42 and records the images inside the subject. After the capsule endoscope 41 is discharged from the subject 40, the portable recording medium 44 is removed from the electronic apparatus 42, and attached to the display device 43. Then, the display device 43 reads out the data recorded in the portable recording medium 44. Since the data delivery between the electronic apparatus 42 and the display device 43 is carried out with the portable recording medium 44 such as a CompactFlash® memory, the subject 40 can move freely even while the capsule endoscope 41 travels inside the subject 40, different from a system where the electronic apparatus 42 and the display device 43 are connected by a cable.

In the above, as the exemplary embodiments of the present invention, the first and the second embodiments are described. The present invention, however, should not be interpreted as to be limited to the above embodiments. Those skilled in the art can reach various embodiments and modifications. For example, the ground potential is separately supplied to each of the first ground terminal 6a and the second ground terminal 7a of the analog circuit block 6 and the digital circuit block 7 in the first and the second embodiments. Alternatively, however, the first ground terminal 6a and the second ground terminal 7a may be electrically connected by a predetermined high impedance member with each other, and further connected to a shared potential supply source. In the above structure, though the first ground terminal 6a and the second ground terminal 7a are electrically connected, the noise level of the first ground terminal 6a is still different from the noise level of the second ground terminal 7a, because of characteristics of the high impedance member placed therebetween. Thus, the advantages of the present invention can still be obtained.

INDUSTRIAL APPLICABILITY

As can be seen from the foregoing, the electronic apparatus and the body insertable apparatus system according to the present invention is useful for a medical observation apparatus which is introduced into a human body and employed for an observation of an examined area, and in particular, suitable for effective suppression of leakage of noise signals generated at the driving of internal electronic circuitry.

The invention claimed is:

1. A body insertable device system, comprising:
a body insertable device capable of being introduced into a subject, which acquires intra-subject information, and transmits radio signals containing the intra-subject information to an outside; and
a receiving apparatus adapted to receive the radio signals transmitted from the body insertable device,
the receiving apparatus including;
a first circuit block adapted to perform analog processing and provided at least with a first ground terminal,
a second circuit block adapted to perform digital processing and provided at least with a second ground terminal and adapted to generate a noise signal of a level higher than a level of a noise signal of the first circuit block on being driven,
a conductive shield member which is adapted to receive a ground potential via the first ground terminal,
a battery provided at least with a third ground terminal, and
a conductive shield board arranged between the first circuit block and the second circuit block and electrically connected to the third ground terminal of the battery.

2. The body insertable device system according to claim 1, wherein
the conductive shield member is configured to house the first circuit block and the second circuit block inside,
the receiving apparatus further comprises a receiving antenna arranged outside the conductive shield member, and
the first circuit block and the second circuit block are adapted to perform predetermined processing on a radio signal received by the receiving antenna.

3. The body insertable device system according to claim 1, wherein the conductive shield member is integrally formed with a casing which houses the first circuit block and the second circuit block.

4. The body insertable device system according to claim 3, wherein
the casing includes:
a case member which is configured to be hollow inside and which defines an outer shape of the casing,
a conductive coating layer which is formed with a coating of a conductive paint on an inner surface side of the casing member, and
a protective layer which is arranged between an inner surface of the casing member and the conductive coating layer.

* * * * *